United States Patent [19]

Schrader et al.

[11] Patent Number: 4,698,437

[45] Date of Patent: Oct. 6, 1987

[54] ALKALI METAL DIALKYLALUMINUM DIHYDRIDES AND SOLUTIONS THEREOF IN AROMATIC HYDROCARBONS

[75] Inventors: Rolf Schrader, Unna; Ulrich Schroeer, Kamen-Methler, both of Fed. Rep. of Germany

[73] Assignee: Schering Aktiengesellschaft, Berlin and Bergkamen, Fed. Rep. of Germany

[21] Appl. No.: 848,265

[22] Filed: Apr. 4, 1986

[30] Foreign Application Priority Data

Apr. 20, 1985 [DE] Fed. Rep. of Germany ....... 3514410

[51] Int. Cl.$^4$ ................................. C07F 5/06
[52] U.S. Cl. ..................... 556/171; 556/170
[58] Field of Search ................. 556/170, 171

[56] References Cited

U.S. PATENT DOCUMENTS

| Re. 25,179 | 5/1962 | Liegler | 556/170 |
| 2,680,059 | 6/1954 | Bragdon | 556/171 |
| 3,506,700 | 4/1970 | Brendel | 556/178 |
| 3,686,248 | 8/1972 | Nelson | 260/448 A |
| 3,696,047 | 10/1972 | Nelson | 252/188 |
| 3,696,136 | 10/1972 | Nelson | 556/171 |
| 4,006,095 | 2/1977 | Hoffman et al. | 556/171 X |
| 4,010,187 | 3/1977 | Nelson | 556/170 X |

OTHER PUBLICATIONS

Zakharkin et al., Zhur. Obsh. Chimii, 32 (3) (1962) 688–960 (translation).

*Primary Examiner*—Helen M. S. Sneed
*Attorney, Agent, or Firm*—Curtis, Morris & Safford

[57] ABSTRACT

Alkali metal dialkylaluminum dihydrides of the formula $$M[Al\ R_{2-n}R'_nH_2]$$

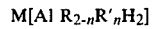

and stable solutions thereof in aromatic hydrocarbons.

6 Claims, No Drawings

ALKALI METAL DIALKYLALUMINUM DIHYDRIDES AND SOLUTIONS THEREOF IN AROMATIC HYDROCARBONS

The present invention relates to alkali metal dialkylaluminum dihydrides and solutions thereof in aromatic hydrocarbons.

Alkali metal dialkylaluminum dihydrides, and especially sodium diethylaluminum dihydride, are known reducing agents and find industrial use as such, particularly for the reduction of carbonyl groups.

Unfortunately, these known compounds, for example, sodium diethylaluminum dihydride, which contain two like alkyl groups, have poor solubility properties in paraffinic solvents, although they permit stable though relatively dilute solutions of about 20 weight percent to be prepared in aromatic hydrocarbons.

Higher solubility in the solvent media mentioned, which would also mean greater reducing power per unit volume, would of course be desirable. It should be borne in mind that it is economically advantageous to be able to ship larger amounts of reducing agent in concentrated solutions.

Published German patent application DAS No. 21 51 495 (=U.S. Pat. No. 3,696,047) has sought to accomplish this by the addition of tetrahydrofuran, for example, which takes advantage of known complexing reactions involving ether oxygen. For example, the concentration of sodium diethylaluminum dihydride in toluene can be increased from 16 weight percent to about 28 percent by the addition of 1.1 weight percent of tetrahydrofuran.

It has now been found that, surprisingly, concentrated solutions of these compounds can be obtained using alkali metal dialkylaluminum dihydrides which have two different alkyl groups therein.

Compounds of the formula

M[Al R$_{2-n}$R'$_n$H$_2$], are the subject matter of the invention. In this formula, R and R' represent different linear or branched alkyl groups each having up to 8 carbon atoms and M represents an alkali metal; n may have a value between 0.1 and 1.9.

Compounds of the formula

Na[AlEt$_{2-n}$n-Bu$_n$H$_2$], where Et is ethyl and n-Bu is n-butyl, and especially Na[AlEt$_{1.6}$n-Bu$_{0.4}$H$_2$], are particularly preferred.

The invention further relates to stable solutions of these compounds, particularly in aromatic hydrocarbon solvents.

Solutions can be prepared with the alkali metal dialkylaluminum dihydrides of the invention wherein no precipitation occurs at room temperature even at a concentration of 60 weight percent in toluene, for instance.

Thus, the active hydrogen content is also high, so that solutions of the compounds of the invention have substantially improved reducing power per unit volume.

Suitable solvents are, in principle, inert paraffinic and aromatic solvents. It is known, for example from U.S. Pat. No. 3,696,047, that, in general, the solubility of pure complex hydrides in paraffinic hydrocarbons is very poor, whereas it is quite good in aromatic hydrocarbons such as benzene. For reasons of stability of the solutions, however, alkylbenzenes such as toluene or xylene are generally preferred as solvents.

The compounds in accordance with the invention can be prepared by methods known in the art, e.g. in U.S. Pat. No. 3,686,248 incorporated herein by reference, for example by reacting sodium hydride with the corresponding dialkylaluminum hydrides. Reference is also made to the state of the art as reflected by the article by Zakharkin et al., Zhurnal Obshchei Khimii 32 (1962) 689-693, entitled "Complexes of Trialkylaluminums and Dialkylaluminum Hydrides with Alkyls of Alkali Metals and Their Hydrides". Dialkylaluminum hydrides which contain some aluminumtrialkyl because of the method by which are are made may also be used.

When solutions are prepared from starting materials which are not pure (for example, old sodium hydride), a filtering step may be necessary. However, the characteristics of the solutions will not be affected thereby.

A better understanding of the present invention and of its many advantages will be had by referring to the following specific examples, given by way of illustration.

EXAMPLE 1

Manufacture of Na[AlEt$_{1.4}$n-Bu$_{0.6}$H$_2$]

A mixture of 60.3 g of diethylaluminum hydride and 42.6 g of di-n-butylaluminum hydride was added over about 10 minutes at room temperature to a suspension of 24 g of sodium hydride in 216 g of toluene with stirring and blanketing with nitrogen. The internal temperature, which is limited by the boiling point of the toluene, rose. Heating was continued for another two hours with refluxing and then the charge was allowed to cool to room temperature. A 37 weight percent solution of the complex compound in toluene with an active hydrogen content of 133 l/g (gas volume is measured at 1 atmosphere and 0° C., i.e. STP) was so obtained.

EXAMPLE 2

Concentration of the Solution of Example 1

By evaporating the toluene from the solution obtained in Example 1, solutions of the compound containing at least 60 weight percent of aluminum in toluene and containing not less than 196 l/g of active hydrogen (STP) were obtained. No precipitation is observed.

EXAMPLE 3

Preparation of Na[AlEt$_{1.7}$n-Bu$_{0.5}$H$_{1.8}$] from technical dialkylaluminum hydrides A mixture of 32.3 g of diethylaluminum hydride and 17.8 g of di-n-butylaluminum hydride contaning a total of 17 g of triethylaluminum and tri-n-butylaluminum was added over about 10 minutes at room temperature to a suspension of 15 g of sodium hydride in 80 g of toluene, with stirring and blanketing with nitrogen. The internal tempertaure rose to about 57° C. Heating was continued for another two hours with refluxing and then the charge was allowed to cool to room temperature. A solution of the compound having an active hydrogen content of 173 l/g (STP) was obtained.

| | | The following compounds were prepared as described in Example 1: | | | | | | | |
|---|---|---|---|---|---|---|---|---|---|
| Example | Compound | Wt. % in toluene | Liters $H_2$/g | Amounts used in g | | | | | |
| | | | | (STP)NaH | Al(Et$_2$H) | Al(i-Bu$_2$H) | Al(n-Bu$_2$H) | Al(n-Oc$_2$H) | Toluene |
| 4 | Na[AlEt$_{1.8}$i-Bu$_{0.2}$H$_2$] | 31 | 120 | 24 | 77.5 | 14.2 | — | — | 258 |
| 5 | Na[AlEt$_{1.5}$i-Bu$_{0.5}$H$_2$] | 35 | 126 | 24 | 64.6 | 35.6 | — | — | 231 |
| 6 | Na[AlEt$_{1.0}$n-Bu$_{1.0}$H$_2$] | 45 | 146 | 12 | 21.5 | — | 35.6 | — | 84 |
| 7 | Na[AlEt$_{0.5}$n-Bu$_{1.5}$H$_2$] | 55 | 163 | 12 | 10.8 | — | 53.3 | — | 62 |
| 8 | Na[AlEt$_{0.1}$n-Bu$_{1.9}$H$_2$] | 45 | 123 | 48 | 8.6 | — | 270.2 | — | 400 |
| 9 | Na[AlEt$_{1.2}$n-Oc$_{0.8}$H$_2$] | 40 | 101 | 12 | 25.8 | — | — | 50.9 | 133 |

EXAMPLE 10

Preparation of K[AlEt$_{1.5}$nBu$_{0.5}$H$_2$]

A mixture of 48.5 g of diethylaluminum hydride and 26.7 g of di-n-butylaluminum hydride was added at room temperature, with stirring and under an inert atmosphere of nitrogen, to a suspension of 30 g of potassium hydride in 170 g of a mixture of xylene isomers over a period of about 10 minutes. The internal temperature, which is limited by the boiling point of xylene, increased. The mixture was heated for an additional two hours under reflux and then left to cool to room temperature. A 38 percent by weight solution of the complex compound in xylene having a content of active hydrogen of 121 l/g (STP) was obtained.

EXAMPLE 11

Preparation of Li[AlEt$_{1.0}$n-Bu$_{1.0}$H$_2$]

A mixture of 64.6 g of diethylaluminum hydride and 106.7 g of di-n-butylaluminum hydride was added at room temperature, with stirring and under an inert atmosphere of nitrogen, to a suspension of 12 g of lithium hydride in 400 g of xylene over a period of about 10 minutes. The internal temperature, which is limited by the boiling point of xylene, increased. The mixture was heated for a further two hours under reflux and then left to cool to room temperature. A 31 percent by weight solution of the complex compound in xylene was obtained having a content of active hydrogen of 114 l/g (STP).

EXAMPLE 12

Preparation of Na[AlMe$_{0.3}$Et$_{1.7}$H$_2$]

A mixture of 13.1 g of dimethylaluminum hydride and 109.8 g of diethylaluminum hydride was added at room temperature, with stirring and under an inert atmosphere of nitrogen, to a suspension of 36 g of sodium hydride in 300 g of a mixture of xylene isomers over a period of about 10 minutes. The internal temperature, which is limited by the boiling point of xylene, increased. The mixture was heated for a further two hours under reflux and left to cool to room temperature. A 35 percent by weight solution of the complex compound in xylene having a content of active hydrogen of 148 l/g (STP) was obtained.

We claim:

1. An alkali metal dialkylaluminum dihydride of the formula $$M[Al\ R_{2-n}R'_nH_2],$$

wherein M is an alkali metal, R and R' are different linear or branched alkyl having up to 8 carbon atoms, and n has a value from 0.1 to 1.9.

2. An alkali metal dialkylaluminum dihydride as in claim 1 which is $$Na[AlEt_{2-n}n\text{-}Bu_nH_2].$$

3. An alkali metal dialkylaluminum dihydride as in claim 1 which is $$Na[AlEt_{1.6}n\text{-}Bu_{0.4}H_2].$$

4. A stable solution of the dihydride of claim 1 in an aromatic hydrocarbon.

5. A stable solution of the dihydride of claim 2 in an aromatic hydrocarbon.

6. A stable solution of the dihydride of claim 3 in an aromatic hydrocarbon.

* * * * *